(12) United States Patent
Schulze-Ganzlin

(10) Patent No.: US 7,628,537 B2
(45) Date of Patent: Dec. 8, 2009

(54) SMALL DENTAL X-RAY APPARATUS AND METHOD FOR POSITIONING AN X-RAY EMITTER

(75) Inventor: Ulrich Schulze-Ganzlin, Lorsch (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 12/071,345

(22) Filed: Feb. 20, 2008

(65) Prior Publication Data

US 2008/0198971 A1 Aug. 21, 2008

Related U.S. Application Data

(60) Provisional application No. 60/907,412, filed on Apr. 2, 2007.

(30) Foreign Application Priority Data

Feb. 21, 2007 (DE) .................. 10 2007 008 962

(51) Int. Cl.
*G03B 42/02* (2006.01)
*H05G 1/02* (2006.01)
(52) U.S. Cl. ...................... 378/170; 378/197
(58) Field of Classification Search .............. 378/168, 378/170, 177, 193, 196, 197, 205, 206, 208
See application file for complete search history.

(56) References Cited

U.S. PATENT DOCUMENTS

| 4,223,228 | A | * | 9/1980 | Kaplan | 378/205 |
| 5,113,424 | A | * | 5/1992 | Burdea et al. | 378/170 |
| 5,598,454 | A | | 1/1997 | Franetzki et al. | |
| 5,828,722 | A | * | 10/1998 | Ploetz et al. | 378/38 |
| 2004/0213382 | A1 | * | 10/2004 | Andell et al. | 378/197 |
| 2006/0066453 | A1 | | 3/2006 | Homanfar et al. | |

* cited by examiner

*Primary Examiner*—Irakli Kiknadze
(74) *Attorney, Agent, or Firm*—Dykema Gossett PLLC

(57) ABSTRACT

A small dental X-ray apparatus has an X-ray emitter 3 fixed to a cantilever 2, which X-ray emitter 3 can be manually adjusted in space relatively to a basic position by means of the cantilever 2. Means 14, 16, 18 are provided for the acquisition of the position and alignment of said X-ray emitter (3) in space.

The method serves to automatically detect deviation of an actual position in space from a target position in space, which deviation is indicated by signalling elements 25 and the operator is informed on the quality of the actual position and on the direction of a change in the actual position which may be required to acquire an improved position.

7 Claims, 2 Drawing Sheets

SMALL DENTAL X-RAY APPARATUS AND METHOD FOR POSITIONING AN X-RAY EMITTER

FIELD OF THE INVENTION

The invention relates to a small dental X-ray apparatus having an X-ray emitter attached to a cantilever, the X-ray emitter being displaceable in space relatively to a basic position by means of the cantilever. The invention also relates to a method for positioning an X-ray emitter of a small dental X-ray apparatus in a target position specified in accordance with at least one predefined item of information, for example, the region to be X-rayed, the treatment to be used, the size of the head, the opinion of the expert involved, and the image detector used.

DESCRIPTION OF THE PRIOR ART

A mobile X-ray diagnostics installation is disclosed in DE 44 14 689 A1, which installation comprises an X-ray emitter, which can be positioned with reference to a subject to be X-rayed by means of an holding arm attached to a column. Furthermore, a device is provided for positioning the X-ray emitter, which device is displaceable via a cantilever connected to the column.

It is known from US 2006/0066453 A1 to align an X-ray emitter by means of an RFID system to a film holder located in the patient's mouth. For this purpose, an antenna array is installed on the X-ray emitter, and these antennas detect an RFID tag attached to the film holder in three-dimensional resolution. The correct alignment of the X-ray emitter to the film holder is displayed on a display device.

When positioning detector media such as a film, a storage plate or digital sensors in the oral cavity for the purpose of generating dental intraoral images, it is important to position the sensor, the tooth region and the radiation source—particularly the tube in this case—in such a way that the desired region is imaged as completely as possible for the respective indication—ie the intended treatment. In addition, it is important that the desired region be trans-irradiated at an optimum angle and that the distances between the various elements be kept within defined limits. Another requirement to be taken into account is that the patient must not suffer any discomfort during generation of the images.

In the prior art, positioning holders have been used as an auxiliary means allowing a fixed association between the X-ray emitter and the image detector. Images of varying quality are achieved depending on the opinion of the technician concerning the correct imaging technology, for example whether the right-angle technique or the half-angle technique should be used, the technical constraints and the experience of the operator.

It is an object of the present invention to assist correct positioning of the X-ray emitter during the creation of an X-ray image.

SUMMARY OF THE INVENTION

Positioning of the X-ray emitter in space can be improved using a small dental X-ray apparatus of the invention, which comprises an X-ray emitter attached to a cantilever, the X-ray emitter being displaceable in space relatively to a basic position by means of the cantilever and means being provided for detecting the position and alignment of the X-ray emitter in space.

Assuming that a patient seated on a chair in a known position holds his head horizontally and looks in a predefined direction, his head position will be substantially defined. Depending on the region to be imaged and on the doctrine held, there is an ideal position for the emitter, ie a position reflecting the correct manner of placing the tube relatively to the patient's head.

The means for detecting the position and the alignment of the X-ray emitter in space can help determine the angle of inclination of the principal axis relative to the horizontal, the angle of rotation of the vertical axis from the head of the X-ray emitter, the distance of the tube outlet from the patient's skin, the distance of the tube outlet from the sensor or the angle of inclination of the sensor relative to the tube, for example, with the help of sensors.

The cantilever advantageously comprises at least two cantilever sections connected via an articulated joint and each articulated joint is provided with a position generator, while the position of the X-ray emitter is determined by means of the signals emitted by the position generators.

Advantageously, a position generator can be mounted on the X-ray emitter, which position generator detects the position and the alignment of the X-ray emitter relative to a known reference position, which can be provided on a fixed part of the cantilever or in the surroundings of the X-ray apparatus. There is thus no necessity to make any structural changes to the cantilever.

Furthermore, means can be provided for detecting the position of a reference point located in the patient's mouth or at a location that depends on the patient's position.

Advantageously, a distance meter can be provided on the X-ray emitter indicating its distance from the patient.

Advantageously, a distance-measuring device for an image detector disposed in the patient's mouth can be provided on the X-ray emitter.

It is particularly advantageous if it is possible to determine not only its distance but also the orientation of the image sensor relative to the principal axis.

According to a development of the invention, a control device can be provided by means of which the actual position of the X-ray emitter can be compared with a predefined target position and at least the coincidence of the actual position with the target position be indicated.

Another object of the invention is to provide a method for positioning an X-ray emitter of a small dental X-ray apparatus in a target position specified in accordance with at least one predefined item of information, for example the region to be X-rayed, the indication (intended treatment), the size of the head, the doctrine held, or the detecting medium, while deviation of an actual position from the target position is determined automatically. The deviation from the target position is indicated by means of signaling elements.

Advantageously, the quality of the actual position and, if appropriate, the direction of a change in position for achieving an improved position can also be indicated to the operator.

Advantageously, the head position of the head of the patient is additionally monitored and taken into consideration in the calculation of the target position. The term "head position" is meant to denote the position or the alignment of the head or, advantageously, both together.

Furthermore, it can be advantageous if permission to effect irradiation is given only when sufficient positional accuracy of the X-ray emitter has been achieved.

BRIEF DESCRIPTION OF THE DRAWINGS

Exemplary embodiments of the invention are shown in the drawings, in which.

DETAILED DESCRIPTION OF AN EMBODIMENT

Figure 1:
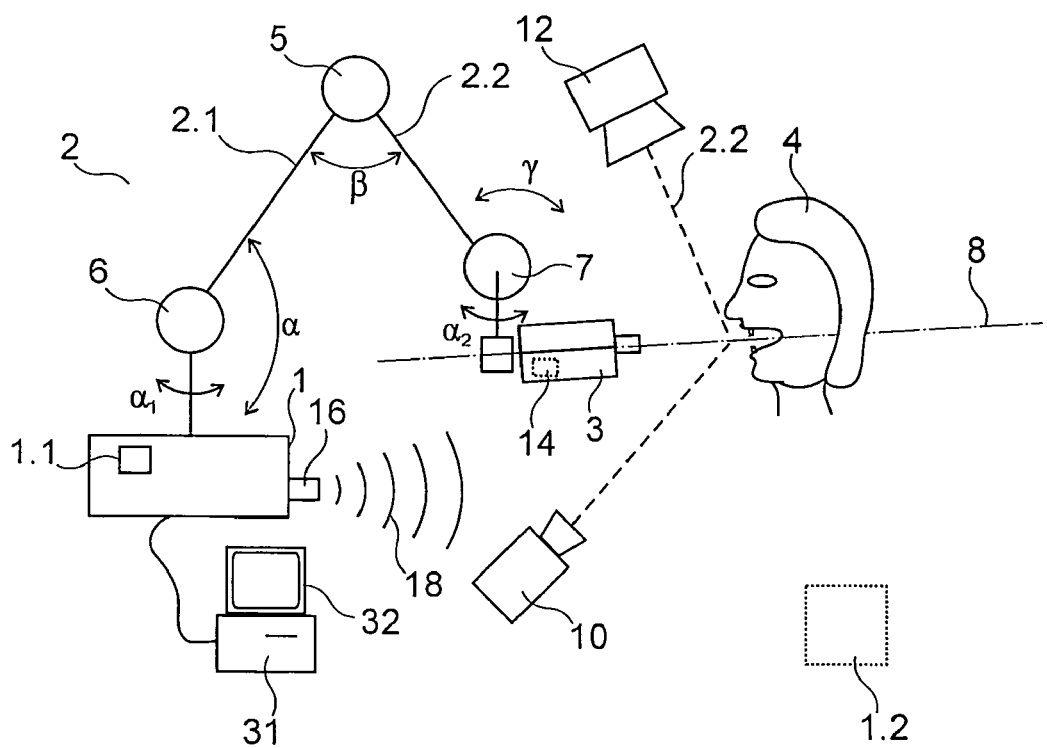
FIG. 1 shows a small dental X-ray apparatus.

FIG. 1 shows a small dental X-ray apparatus. That end of the cantilever 2 which is near a fixed base part 1 is attached to the base part, an X-ray emitter 3 being attached to that end of the cantilever 2 which is remote from the base part. The X-ray emitter 3 can be displaced towards a patient's head 4 by means of the cantilever 2 and the X-ray emitter can be brought into various angular positions relative to the patient's head 4.

For this purpose, the cantilever 2 comprises two cantilever sections 2.1, 2.2, which are interconnected by means of an articulated joint 5. In addition, the cantilever could likewise be attached to the base part 1 by means of an articulated joint 6 and the X-ray emitter 3 could likewise be attached by means of an articulated joint 7 to section 2.2 of the cantilever 2. Such cantilevers are adequately known in the prior art.

With the help of these cantilevers, it is possible to align the X-ray emitter 3 relatively to the patient's head 4 and also to adjust a required obliquely positioned principal axis 8, which is shown here as a substantially horizontally aligned X-ray emitter 3.

Figure 2:
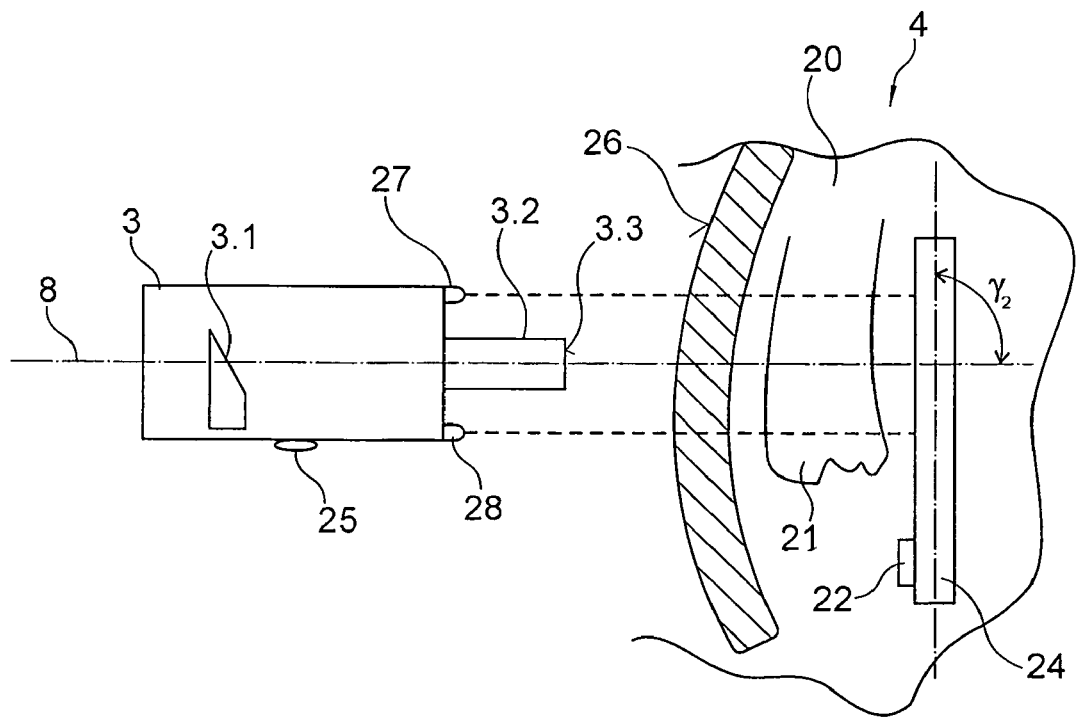
FIG. 2 shows a detail of an X-ray emitter.

As shown in detail in FIG. 2, a focal point 3.1, which is located in the X-ray emitter 3 and corresponds to the point of origin of the X-ray emission, can be used to closely define the position of the X-ray emitter 3. The principal axis 8 of the X-rays emitted from the focal point 3.1 can be used to closely define the alignment of the X-ray emitter 3. This principal axis 8 coincides with a tube axis of a tube 3.2 surrounding the X-ray beam as a part of the X-ray emitter housing, and runs approximately through the center of a tube outlet 3.3 facing the patient.

By default, the distance between the focal point and the tube outlet is 3.38×2.54 cm. or in case of a top piece (not shown) 12×2.54 cm. The diameter of the tube at the tube outlet 3.3 is not more than 6 cm.

Detection of the position and alignment of the X-ray emitter in space can thus comprise to determining the position of the focal point 3.1 and to determining the alignment of the principal axis 8.

For detecting the position of the patient's head 4 or the position of the X-ray emitter 3, measuring cameras 10, 12, shown in FIG. 1, are provided, which provide measuring results via an evaluation unit.

The cameras 10, 12 are also suitable as a detection system with which it is possible to determine the occlusal plane of the upper jaw from the position and alignment, and the size of the patient's head. The eyes, being easily detectable, can serve as orientation.

Figure 4:
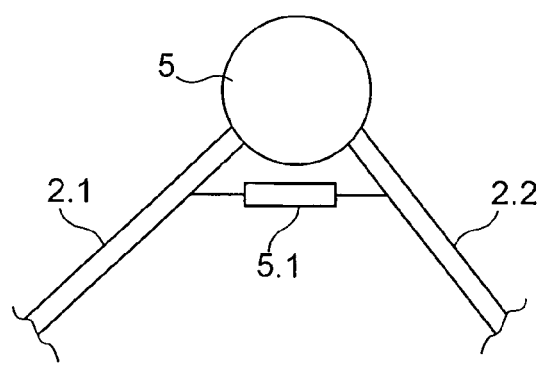
FIG. 4 shows an articulated joint with a position generator.

Each of the articulated joints 5, 6, 7 can be provided with a position generator 5.1, shown in FIG. 4, which is designed, for example, as an angular rotation transmitter. The angle α between the cantilever section 2.1 and the base part 1, angle β between the two cantilever sections 2.1 and 2.2, and angle γ between the cantilever section 2.2 and the X-ray emitter 3 can be determined by means of the angular rotation transmitter 5.1 in the articulated joints 5, 6, 7, since the aspect ratios of the cantilever sections 2.1, 2.2 and the X-ray emitter 3 are known. In addition, the angles of rotation α1 und α2 at the base part 1 or at the X-ray emitter 3 relative to the perpendicular can be detected and evaluated.

The position of the X-ray emitter can be determined from the signals emitted by the position generators and from the known geometric relationships.

It is also possible to mount a position generator 14 on the X-ray emitter 3, which position generator specifies the position and the orientation of the X-ray emitter 3 relative to a known reference position 1.1; 1.2, which can be provided on a fixed base part of the cantilever or in the surroundings of the X-ray apparatus. Alternatively, the position generator can be used to determine this location and the alignment of the X-ray emitter 3, for example, by means of a direction finding station 16 mounted on the base part 1 emitting a localizing signal 18.

The measuring cameras 10, 12 are the means for detecting the location of a reference surface located in the patient's mouth or at a reference position present at a location that depends on the patient's position. The reference surface can be, for example, the occlusal plane of the teeth, the location of which is determined by means of the measuring cameras 10, 12.

FIG. 2 shows that a distance meter 28 can be provided on the X-ray emitter 3 for measuring its distance from the patient 4, for example, from the skin 26 of the patient 4. The distance meter 28 provides a warning, for example, when the distance between the tube outlet 3.3 and the skin surface 26 of the patient 4 is too long. Said distance should normally be between 0 and 5 cm.

Advantageously, a distance-measuring device 27 can also be provided on the X-ray emitter for measuring its distance from an image detector 24 disposed in the patient's mouth, as disclosed, for example, in WO 2006/023674 A1.

Advantageously, the distance-measuring device 27 is designed in such a way that it can determine not only the distance but also the orientation of an image detector 24 relative to the principal axis 8 of the X-ray emitter 3. For this purpose, a marker 22 is mounted on the image detector 24, and the location and orientation of this marker relative to the principal axis 8 can be detected by means of the distance-measuring device 27. In particular, a tilt angle γ2 relative to the principal axis 8 is also detected.

The quality of the actual position and, if necessary, the direction for a required change of position to create an improved position is communicated to the operator by means of a signaling element 25.

FIG. 1 further shows that the actual position of the X-ray emitter 3 as determined is compared with a predefined target position by means of a control device 31, here in the form of a PC. The coincidence of the actual position with the target position can be indicated on a display unit 32. It is also possible to provide display means on the X-ray emitter 3 itself for displaying the position of the latter.

Figure 3:
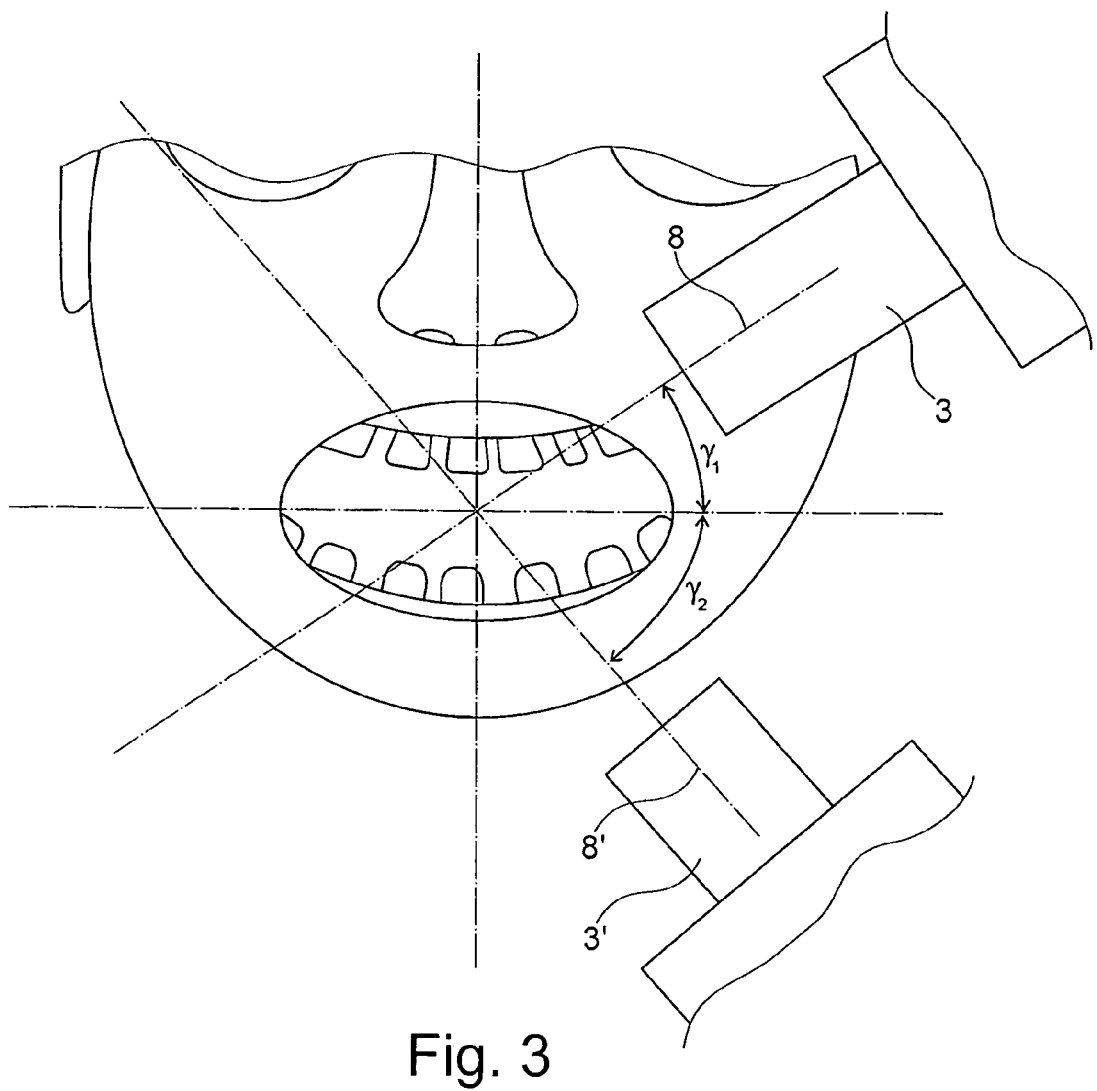
FIG. 3 shows different positions of the X-ray emitter relative to a patient.

It is of particular significance that the X-ray emitter 3 can be manually positioned freely in space relatively to the patient's head in order to X-ray the mouth cavity either from the cheek surfaces or from the front, the image detector 24 being disposed behind the teeth 21 (FIG. 2). In addition to using a horizontal orientation of the principal axis 8 of the X-ray emitter 3, it will also be necessary to direct the X-ray emitter towards the mouth cavity obliquely from above or obliquely from below, in which case it will be possible to adjust and detect an angular range γ1, γ2 of the head 8, 8' of the X-ray emitter relative to the horizontal, see the schematic illustration shown in FIG. 3.

Although the small X-ray devices disclosed in the prior art have a cantilever which enables such positioning of the X-ray emitter, it is additionally particularly important for it to be possible to document the exact positioning of the X-ray emitter, namely without intervention by the operator.

The position data can be stored as determined in an archive, together with the image, for use for documentation purposes. From these data it is possible to derive post-hoc optimizations of the positioning specification for the target position by taking into account some special habits of the user. It is thus possible to use a self-learning system, such as e.g. neuronal networks or Fuzzy Logic.

Since the geometric situation of the chair and the X-ray apparatus or its emitter is known beforehand, the system comprising the X-ray emitter 3, which is connected to the patient-position detecting system and a patient management system, can determine an ideal target position of the X-ray emitter 3 from available information concerning the region to be X-rayed, the indication, from the age and possible head size of the patient, the doctrine to be adopted, and the type of detector medium to be used: for example, flexible-rigid, large-small, etc.

Furthermore, the system detects any deviation of the actual position from the target position. The user receives suitable feedback signals, e.g. by means of optical signaling elements such as LEDs directly on the head of the emitter being moved by the operator, or by means of an acoustic feedback signal. In addition, the position of the patient's head can be monitored and taken into consideration in the calculation of the actual position. Such monitoring can be carried out using, for example, one or more cameras 10, 12 (FIG. 1).

The deviation of an actual position in space from the target position in space can be detected and displayed by means of signal elements using a method for detecting the position of an X-ray emitter of a small dental X-ray apparatus in a target position, which is determined taking into account at least one predefined documented item of information, for example, the region to be X-rayed, the indication, ie the intended treatment, the size of the patient's head, the doctrine followed, the detector medium, etc. Furthermore, it is possible to inform the operator concerning the quality of the actual position and, if appropriate, the direction of a change in the actual position required for achieving an improved position.

A graphic display with corresponding indicating elements can also be used in addition to, or instead of, the LEDs.

It is also possible to take into consideration the position of the patient's head in the calculation of the target position.

Alternatively, it is possible to correct the actual position according to the position of the patient's head if this differs from a predefined position.

The method can be used, for example, to ensure that the X-ray emitter 3 permits release of the radiation only on achieving sufficient positional accuracy of the X-ray emitter 3 relative to the patient 4 and optionally relative to the image detector 24. Vice versa, the release of radiation can be blocked in the case of grossly incorrect positioning, e.g. if the distance of the X-ray emitter from the patient is excessively long. However, this technology should be understood mainly as one providing auxiliary means for assisting the operator.

The invention claimed is:

1. A small dental X-ray apparatus, comprising an X-ray emitter (3) fixed to a cantilever (2) for adjustable positioning in space, and means (14, 16, 18) for acquisition of position and alignment of said X-ray emitter (3) in space, said means including a position generator (14) mounted on said X-ray emitter for ascertaining position and alignment of said X-ray emitter (3) relative to a known reference position (1.1, 1.2) provided on a base part (1) of said cantilever (2) or in surroundings.

2. The X-ray apparatus according to claim 1, wherein said cantilever (2) comprises at least two sections (2.1, 2.2) interconnected via an articulated joint (5-7), each articulated joint (5-7) being provided with a position generator (5.1), and the position of the X-ray emitter (3) is determined from the signals delivered by the position generators (5.1).

3. The X-ray apparatus according to claim 1, including means (10,12) for the acquisition of the position of a reference point located in the mouth of the patient or at a position dependent on the position of the patient.

4. The X-ray apparatus according to claim 1, including a distance meter (28) on said X-ray emitter for measuring the distance of a focal point (3.1) from the patient (4; 26).

5. The X-ray apparatus according to claim 1, including a distance measuring device (27) on said X-ray emitter for ascertaining the distance of a focal point (3.1) from an image detector (24) disposed in the mouth of the patient.

6. The X-ray apparatus according to claim 5, wherein it is possible to determine not only the distance but also the alignment of said image detector (24) with reference to a principal axis (8) of said X-ray emitter (3).

7. The X-ray apparatus according to claim 1, including control equipment (31) by means of which the actual position of said X-ray emitter (3) is compared with a target position and at least the coincidence of the actual position with the target position is indicated.

* * * * *